United States Patent [19]
Lasser

[11] 3,953,378
[45] Apr. 27, 1976

[54] MINERAL CARRIER FOR VOLATILE SUBSTANCES AND PROCESS FOR PREPARING SAME

[75] Inventor: Bruno T. Lasser, Givrins, Switzerland

[73] Assignee: Firmenich S.A., Geneva, Switzerland

[22] Filed: Nov. 18, 1974

[21] Appl. No.: 525,021

[30] Foreign Application Priority Data
Nov. 21, 1973 Switzerland.......................... 16439/73
Apr. 5, 1974 Switzerland.......................... 4847/74

[52] U.S. Cl................................. 252/522; 106/109; 106/111
[51] Int. Cl.² ................................................ A61K 7/46
[58] Field of Search ............. 252/522; 106/109, 111

[56] References Cited
UNITED STATES PATENTS

| 3,316,901 | 5/1967 | Smith | 106/111 |
| 3,664,963 | 5/1972 | Pasin | 252/522 |
| 3,772,215 | 11/1973 | Gould et al. | 252/522 |
| 3,780,195 | 12/1973 | Balassa | 252/522 |
| 3,819,388 | 6/1974 | Cornwell | 106/109 |

OTHER PUBLICATIONS

F. Winter, Handbuch der Gesamten Parfümerie und Kosmetic, Springer Verlag, Vienna, p. 288, 1952.

Primary Examiner—C. Davis
Attorney, Agent, or Firm—Pennie & Edmonds

[57] ABSTRACT

Mineral carrier destined to incorporate a volatile substance, in particular a perfuming ingredient or a mixture of perfuming ingredients, a bactericide or an insecticide, or at least one perfuming ingredient together with a bactericide or an insecticide.

Process for preparing said carrier.

Process for preparing a perfumed gypsum article and said perfumed article.

12 Claims, No Drawings

MINERAL CARRIER FOR VOLATILE SUBSTANCES AND PROCESS FOR PREPARING SAME

SUMMARY OF THE INVENTION

The invention relates to a process for preparing a mineral carrier destined to incorporate a volatile substance, which comprises hydrating a partially dehydrated mineral material by means of a diluted aqueous solution of a polyalkylidene-glycol or a monoalkoxy derivative thereof.

The invention also relates to a process for preparing a perfumed article, which comprises incorporating a perfuming ingredient, or a mixture of perfuming ingredients, into a mixture of plaster and a diluted aqueous solution of a polyalkylidene glycol or a monalkoxy derivative thereof, before the said mixture hardens.

The invention finally relates to a perfumed gypsum article whenever prepared in accordance with the hereinabove mentioned process.

BACKGROUND OF THE INVENTION

Perfumes find nowdays an extremely broad utilisation For example, cosmetic preparations, soaps, detergents and household materials in general represent the most currently perfumed articles found on the market. New types of materials liable to be perfumed, and thus rendered commercially more attractive, are constantly offered to the consumer Materials as varied as wax, paper, cardboard, synthetic resins, plastic or even metal are often considered suitable supports destined to incorporate perfumes or various volatile substances such as insecticides or bactericides.

Gypsum can also be taken into consideration for the very same purpose. Its use as carrier for perfumes was suggested in the past and the preparation of perfumed gypsum articles was already described [see F. Winter, "Handbuch der gesamten Parfumerie und Kosmetic," Springer Verlag, Vienna 1952, p, 288]. Hitherto, however, the manufacture of perfumed gypsum articles was not developed industrially.

This fact is rather surprising in view of the fact that:
gypsum is an extremely cheap and readily available material;
the manufacture of gypsum, which consists simply in mixing plaster and water in adequate proportions, does not necessitate complex apparatus or expensive processes;
the perfume incorporation into the gypsum mass can be effected by simply impregnating the gypsum article with a diluted perfume, e.g., an alcoholic solution thereof; or
the said incorporation can also be carried out, in accordance with the above cited literature, by mixing the required amount of perfume with the plaster-water mixture.

The first incorporation mode hereinabove described is however unsatisfactory as the proportion of incorporated perfume cannot be precisely measured and perfume cannot be homogeneously distributed in the gypsum mass. The said process moreover is relatively slow and the proportion of incorporated perfume does not exceed 3 to 5 % of the total weight of the perfumed material.

The second of the above mentioned incorporation modes is also unsatisfactory as shown by the following investigation. In order to determine the possible feasibility of the said process it was made use of model substances, these being chosen according to their widespread occurrence as ingredients in perfume compositions and their more or less pronounced lipophilicity or hydrophilicity.

The following three compounds were used as models:
phenylethyl alcohol: strongly hydrophile
diethyl phthalate : strongly lipophile and
isobornyl acetate : hydrophile/lipophile The obtained results — see Test No. 1 — clearly show that, in the three cases, the desired ingredient could be easily incorporated into the gypsum mass in a proportion of up to 5 % (parts by weight). Higher proportions cannot be incorporated, the mass "sweats" and presents an irregular texture.

Test No. 1

A plaster base was prepared by adding portionwise 65 g of powdered plaster (Platre de Paris) to 35 ml of water under vigorous stirring. 1 g of phenylethyl alcohol was then added to the vigorously stirred mass, and its complete absorption took place within 3 minutes. The thus obtained mixture was then rapidly poured into moulds and let to harden at room temperature.

The above process was then repeated, by adding 2, 5 and 10 g respectively, of phenylethyl alcohol to the above plaster base (100 g). It was observed that the alcohol was completely incorporated into the mass, whenever added in the proportion of 2 and 5 g, whereas by adding it in the proportion of 10 g, a certain amount of it remained on the surface of the gypsum mass even after hardening and drying.

Analogous tests were then carried out by using 1, 2, 5 and 10 g of isobornyl acetate and equal amounts of diethyl phthalate, respectively.

In both cases, it was observed that amounts of 1, 2 and 5 g were completely incorporated, whereas the 10 g sample was only partially absorbed in the gypsum mass.

It was then tried to incorporate a perfume composition into the gypsum mass, by using the same procedure as given above – see Test No. 2. In this case too, only proportions up to 5 % (parts by weight) were satisfactorily incorporated.

Test No. 2

A perfume composition of a "Fougère" type was first prepared, by mixing the following ingredients (parts by weight):

| | |
|---|---:|
| Phenylethyl alcohol extra | 70 |
| Isoeugenol | 25 |
| Lavender oil | 120 |
| Linalyl acetate extra | 75 |
| Lemon oil | 70 |
| Portugal Florida | 50 |
| Geraniol | 120 |
| Coumarine | 20 |
| Citronellal | 5 |
| Cedar wood oil | 25 |
| Patchouli oil | 120 |
| Dimethyl-hydroquinone | 15 |
| Petitgrain oil | 15 |
| Amyl-cinnamic aldehyde | 30 |
| Absolute oak moss 10 %* | 40 |
| α-Iso-methylionone | 80 |
| Decylic aldehyde 10 %* | 20 |
| Cinnamic aldehyde 10 %* | 100 |
| Total | 1000 |

*in diethyl phthalate

The above composition was then incorporated into a plaster-water mixture in accordance with the method given in Test No. 1, by using samples of 1, 2, 5 and 10 g, respectively, of the said perfume composition per 100 g of the plaster-coater mixture.

In the first three cases, the perfume composition was completely absorbed in the gypsum mass, whereas by the addition of the 10 g sample, a certain amount of the said composition remained on the surface of the mass even after its hardening and drying.

Therefore, the prior art seems to discourage the man skilled in the art to manufacture perfumed gypsum articles, more precisely those which have to incorporate a relatively high proportion of perfume – e.g., higher than 10%.

The present invention represents a solution to this problem.

PREFERRED EMBODIMENTS OF THE INVENTION

It has now been surprisingly discovered that, in the manufacture of a gypsum carrier, it was possible to overcome the above mentioned difficulties, by preliminary dissolving a certain amount of polyalkylidene-glycol, or a monoalkoxy derivative thereof, in the amount of water necessary to the hydration of plaster.

One of the objects of the present invention is a process for preparing a mineral carrier destined to incorporate a volatile substance, which comprises hydrating a partially dehydrated mineral material by means of a diluted aqueous solution of a polyalkylidene-glycol or a monoalkoxy derivative thereof.

The effect of the polyalkylidene-glycols or monoalkoxy derivatives thereof, called also "glycols" hereinafter, essentially consists in promoting a homogenous distribution of the perfume into the gypsum mass, as well as a complete dissolution of the said perfume in the amount of water used for the hydration of plaster. It can be assumed that the "glycols" essentially act as a binding agent upon the lipophilic ingredients of a given perfume composition, upon, e.g., compounds such as high molecular weight ketones and esters or terpene hydrocarbons.

Moreover, the "glycols" do not exert any major influence on the hardening of plaster and contribute as well to a more uniform evaporation of the incorporated perfume.

It has also been found that a mineral carrier prepared in accordance with the above defined process of the invention could absorb high proportions of a given perfume by simply impregnating it with the chosen perfume composition. This method proved to be completely unsatisfactory, when applied to a mineral carrier, e.g., gypsum, which did not contain any of said "glycols."

Suitable glycols include polyethylene-glycol, polypropylene-glycol or monoalkoxy derivatives thereof such as the monoethyl ether derivative of polypropylene-glycol, polyethylene-glycol lauryl ether or polyethylene-glycol nonylphenol ether. These glycols can be used individually or as mixtures comprising at least two of them. By using said glycols in accordance with the invention it is now possible to incorporate perfumes in proportions as high as 10 to 25 % of the total weight of the perfumed mineral article.

Polyethylene-glycol (PEG) is the preferred glycol. It is easily available on the market at a relatively low price and in large amounts. It is made available in a variety of quality depending on its viscosity, its solubility in water or its physical state.

In accordance with a preferred embodiment of the process of the present invention, a PEG having an average molecular weight comprised between 200 and 35,000, preferentially between 6000 and 35,000, more preferentially of the order of 20,000 is used.

PEG 20,000, which is completely soluble in water at room temperature, has the great advantage of not including any foaming in the course of the gypsum manufacture. It is chemically stable, non toxic, inert towards the commonly used perfume ingredients and as such does not alter the olfactive properties of the incorporated perfume.

The proportions of the glycols used in accordance with the present invention may vary within a wide range. PEG 20,000 for example can be advantageously used in the proportions of 5 to 80 % of the weight of the perfume which has to be incorporated into the gypsum article. Whenever PEG 20,000 is used, a preferential proportion is of about 50 %.

In accordance with a preferred embodiment of the process of the present invention, the glycols are first diluted in the amount of water necessary to the hydration of plaster, whereupon the required amount of plaster is added to the obtained solution, Finally the perfume is added to the semi-liquid mass thus obtained. The obtained mixture is further stirred until complete incorporation of the perfume, poured into moulds and finally let to harden and to dry in accordance with usual techniques.

A further object of the present invention is a process for preparing a perfumed gypsum article, which comprises incorporating a perfuming ingredient, or a mixture of perfuming ingredient, into a mixture of plaster and a diluted aqueous solution of polyalkylidene glycol, or a monoalkoxy derivative thereof, before the said mixture hardens.

In the present specification the term "perfume" is deemed to define a single perfuming ingredients as well as a perfume composition.

It was established that a mineral carrier, whenever prepared in accordance with the invention, could also advantageously be used as a support for volatile substances other than perfumes, for example for bactericides, insecticides or mixtures of at least one perfuming ingredient together with an insecticide or a bactericide.

Typical mineral carriers prepared in accordance with the invention also include cement and calcium carbonate.

The present invention will be better illustrated by the following Examples.

EXAMPLE 1

The following chemicals were used for the preparation of a perfumed gypsum article.

| Test | Chemical | Available from | Structural Characterization |
|---|---|---|---|
| 1 | ARKOPAL N080 | Hoechst AG | Polyethylene-glycol nonyl-phenol ether |
| 2 | DIONIL SM 100 | Chem.Werke Huls AG | Alkylolamide-polyethylene-glycol ether |
| 3 | MARLAMID M 1218 | Chem.Werke Huls AG | Alkylolamide |
| 4 | MARLOX FP 30/100 | Chem.Werke Huls AG | Monoethoxylated polypropylene-glycol |

-continued

| Test | Chemical | Available from | Structural Characterization |
|---|---|---|---|
| 5 | MARLON A 375 | Chem.Werke Huls AG | Alkylbenzene sulfonate |
| 6 | MARIPAL FS | Che.Werke Huls AG | Polyethylene-glycol diester |
| 7 | PEG 20000 | Hoechst AG | Polyethylene-glycol |

The above mentioned chemicals were choosen by virtue of their "binding" character towards both lipophilic and hydrophilic types of perfume constituents. All of these chemicals display a so-called "tensio-active" character.

The perfumed gypsum article was prepared as follows: 52 g of plaster (Plâtre de Paris) were added by portions, under good stirring, to a solution, or suspension, of 8 g of one of the above cited chemicals in 28 ml of water. 12 g: of the perfume composition described in Test No. 2 were then incorporated into the homogeneous semi-liquid mass under stirring. The thus obtained mixture was then rapidly poured into moulds, let to harden and dried in accordance with usual techniques.

The observed results are summerized hereinafter.

| Test | Perfume Incorporation | Observations |
|---|---|---|
| 1 | complete | — |
| 2 | partial | the plaster-water mixture did not harden after 16 h |
| 3 | no incorporation | — |
| 4 | complete | — |
| 5 | complete | the plaster-water mixture did not harden, even 20 h after its preparation |
| 6 | partial | — |
| 7 | complete | — |

The results given in the above Table clearly indicate that among the variety of known tensio-active chemicals the "glycols" possess the most interesting and useful properties.

EXAMPLE 2

Three different perfume compositions were used for the preparation of a perfumed gypsum article.

A. Fougère type perfume composition (see Test No. 2)

b. "Pine" type perfume composition

| Ingredients | Parts by weight |
|---|---|
| Isobornyl acetate | 400 |
| Liquid bornyl acetate | 100 |
| Linalol extra | 30 |
| Lavandin oil | 20 |
| Linalyl acetate extra | 90 |
| Juniper oil | 30 |
| Eucalyptol | 15 |
| Petitgrain oil | 20 |
| Siberian pine oil | 200 |
| Rosemary oil | 40 |
| α-Phenylethyl acetate | 10 |
| Coumarin | 25 |
| Methylnonylacetic aldehyde 10 %* | 10 |
| ter-Butyl-cyclohexyl acetate | 10 |
| Total | 1000 |

*in diethyl phthalate

C. "Fruity" type perfume composition

| Ingredients | Parts by weight |
|---|---|
| Benzaldehyde | 500 |
| 4-Methylbenzaldehyde | 125 |
| Amyl butyrate | 50 |
| Ethyl butyrate | 37 |
| Ethyl methyl-phenylglycidate | 25 |
| Vanillin | 25 |
| Benzyl acetate | 15 |
| Ethyl oenanthate | 12 |
| Anisic aldehyde | 10 |
| Anisyl acetate | 6 |
| Cinnamic aldehyde | 5 |
| Eugenol extra | 2 |
| Diethyl phthalate | 188 |
| Total | 1000 |

The perfumed gypsum article was prepared as follows: 65 g of plaster were added to a solution of 10 g of PEG 20,000 in 35 ml of water, in accordance with the process of Example 1. 5, 10 and 15 g samples, respectively, of perfume composition A were then incorporated into the mass under stirring. The thus obtained mixture was then poured into moulds and let to harden.

In all the above cases, it was observed that the perfume composition as totally incorporated.

The above process was repeated, in the same conditions, with perfume compositions B and C, respectively. In both cases too, analogous results were observed.

EXAMPLE 3

A perfume composition of a "Citron Fantaisie" type was first prepared, by mixing the following ingredients (parts by weight):

| Ingredient | Parts |
|---|---|
| Cedar wood oil | 100 |
| Bergamot oil | 150 |
| Lavandin oil | 200 |
| Benzyl acetate | 30 |
| Benzyl salicylate | 10 |
| Amyl salicylate | 10 |
| Coumarin | 30 |
| Lemon oil | 160 |
| Litsea Cubeba | 60 |
| Ylang oil | 10 |
| Citronella oil | 30 |
| Isobornyl acetate | 100 |
| Diethyl phthalate | 110 |
| Total | 1000 |

The thus obtained perfume composition was then used for the preparation of a perfumed gypsum article as indicated hereinafter: 72 g of plaster were added to a solution of 8 g of PEG 20,000 in 40 ml of water in accordance with the process of Example 1. The obtained mixture was then poured into a cylindrical mould ($\phi$ 5.5 cm), let to harden and dried as usual.

Three aliquotes of about 500 mg each were taken from different sections of the cylindrical mould:

| | | |
|---|---|---|
| 1. | the upper face: | in contact with surrounding air |
| 2. | the middle: | at half height |
| 3. | the lower face: | in contact with the walls of the mould. |

Each of the above samples was then finely ground and extracted with 1 ml of absolute ethanol. The obtained organic extracts were then separately analyzed by vapour phase chromatography (CAMBOWAX column; 70°C; 4 m) and shown to possess the same composition relative to their perfuming ingredients.

EXAMPLE 4

A perfumed gypsum article, prepared as indicated in Example 3, was let to stand at 20°C for 4 months, in a well aerated thermostatic oven. Three aliquotes of about 500 mg each were taken from different sections of the cylindrical mould:

| | | |
|---|---|---|
| 1. | the upper face: | in contact with the surrounding air |
| 2. | the middle: | at half height |
| 3. | the lower face: | in contact with the walls of the mould. |

The three samples were subjected to the same treatment as indicated in Example 3 and in this case too they showed the same composition relative to each other.

Examples 3 and 4 clearly show two of the main advantages presented by the perfumed gypsum article prepared in accordance with the process of the invention, i.e.:

a. homogeneous distribution and
b. slow and uniform evaporation of the perfume.

EXAMPLE 5

The perfuming composition described in Example 3 was used for the preparation of a perfumed cement article as follows:

To 4 g of commercial grade cement and 12 g of sand, there was added a solution of 4 g of PEG 20,000 in 8 ml water. The thus obtained mass was intimately mixed and added of 0.8 g of the perfuming composition and poured into moulds. The perfumed cement mass hardens within 3 or 4 days. A perfectly homogeneous article was obtained.

Analoguous results were observed by using mixtures of cement and sawdust instead of the aforementioned mixture of cement and sand. The proportions used (parts by weight) were as follows:

| | (I) | (II) |
|---|---|---|
| Cement | 12 | 4 |
| Sawdust | 4 | 12 |
| PEG 20,000 | 4 | 4 |
| Water | 18 | 18 |
| Perfume | 0.8 | 0.8 |

EXAMPLE 6

52 g of plaster powder (Platre de Paris) were added to a solution of 8 g of PEG 20,000 in 28 g of water. 12 g of Pyrethrum (25 % extract, available from Siber Hegner Co., Zurich, Switzerland) were then added to the plaster mass under stirring and the mixture was let to harden in moulds. A homogeneous distribution of pyrethrum was observed.

EXAMPLE 7

12 g of dichloro-diphenyl-trichloroethane (DDT), available from Ciba-Geigy, Basel, Switzerland, in 8 g of PEG 20,000 was slowly warmed up to about 60°–65°C. 28 g of water were then added to the obtained solution, followed by 52 g of plaster. The homogeneous mixture was poured into moulds and solidifies within 1 hour. A homogeneous distribution of DDT was observed.

EXAMPLE 8

A mineral carrier destined to incorporate a volatile substance was prepared as follows:

65 g of plaster (Plâtre de Paris) were slowly added under good stirring to a solution of 10 g of PEG 20,000 in 35 ml of water. The obtained mass was then poured into moulds and let to harden overnight at room temperature.

What is claimed is:

1. A process for preparing a gypsum carrier destined to have incorporated therein a perfume or mixture of perfumes comprising hydrating plaster with an effective amount to cause hydration of a dilute aqueous solution of a glycol selected from polyethylene glycol, polypropylene glycol, polyethylene glycol monoethyl ether, polyethylene glycol lauryl ether, polyethylene glycol nonylphenyl ether and mixtures thereof.

2. The process according to claim 1 wherein the glycol is polyethylene glycol.

3. The process according to claim 2 wherein the polyethylene glycol possesses an average molecular weight of between about 200 and about 35,000.

4. The process according to claim 3 wherein the polyethylene glycol possesses an average molecular weight of between about 6,000 and about 35,000.

5. A process for preparing a perfumed gypsum article comprising mixing plaster with an effective amount to cause hydration of a dilute aqueous solution of a glycol selected from polyethylene glycol, polypropylene glycol, polyethylene glycol monoethyl ether, polyethylene glycol lauryl ether, polyethylene glycol nonylphenyl ether and mixtures thereof and incorporating into the mixture a perfume or mixture of perfumes.

6. The process according to claim 5 wherein the glycol is polyethylene glycol.

7. The process according to claim 6 wherein the polyethylene glycol possesses an average molecular weight of between about 200 and about 35,000.

8. The process according to claim 6 wherein the polyethylene glycol possesses an average molecular weight of between about 6,000 and 35,000.

9. The process according to claim 8 wherein the polyethylene glycol is used in the proportions of 5 to 80 percent of the weight of the perfume material incorporated in the gypsum article.

10. The process according to claim 5 wherein the amount of perfume or mixture of perfumes comprises up to 25 percent by weight of the formed article.

11. The process according to claim 5 wherein the glycol is polyethylene glycol having an average molecular weight of between about 6,000 and 35,000 and wherein the amount of perfume or mixture of perfumes is up to 25 percent by weight of the formed article.

12. The process of claim 10 wherein the polyethylene glycol is used in the proportions of 5 to 80 percent of the weight of the perfume material.

* * * * *

UNITED STATES PATENT OFFICE
CERTIFICATE OF CORRECTION

Patent No. 3,953,378　　　Dated April 27, 1976

Inventor(s) Bruno T. Lasser

It is certified that error appears in the above-identified patent and that said Letters Patent are hereby corrected as shown below:

Column 2, line 11, "that, in the" should read -- that, in all the --. Column 4, lines 9 and 10, "not including" should read -- be not inducing --. Column 5, line 21, "12 g:" should read -- 12 g --. Column 6, line 25, "as" should read -- was --.

Signed and Sealed this

Fifth Day of October 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,953,378             Dated April 27, 1976

Inventor(s) Bruno T. Lasser

It is certified that error appears in the above-identified patent and that said Letters Patent are hereby corrected as shown below:

Column 2, line 11, "that, in the" should read -- that, in all the --. Column 4, lines 9 and 10, "not including" should read -- not inducing --. Column 5, line 21, "12 g:" should read -- 12 g --. Column 6, line 25, "as" should read -- was --.

This certificate supersedes Certificate of Correction issued October 5, 1976.

Signed and Sealed this

Twenty-first Day of December 1976

[SEAL]

Attest:

RUTH C. MASON
Attesting Officer

C. MARSHALL DANN
Commissioner of Patents and Trademarks